(12) United States Patent
Wing et al.

(10) Patent No.: US 6,210,442 B1
(45) Date of Patent: Apr. 3, 2001

(54) IMPLANT FOR VERTEBRAL BODY FUSION

(75) Inventors: Charles Wing, Wurmlingen; Guntmar Eisen; Robert Schultz, both of Tuttlingen, all of (DE)

(73) Assignee: Aesculap AG & Co. KG, Tuttlingen (DE)

( * ) Notice: Subject to any disclaimer, the term of this patent is extended or adjusted under 35 U.S.C. 154(b) by 0 days.

(21) Appl. No.: 09/226,800

(22) Filed: Jan. 7, 1999

Related U.S. Application Data

(63) Continuation of application No. PCT/EP97/03730, filed on Jul. 12, 1997.

(30) Foreign Application Priority Data

Jul. 15, 1996 (DE) .............................................. 196 28 473

(51) Int. Cl.$^7$ ...................................................... A61F 2/44
(52) U.S. Cl. ......................................................... 623/17.11
(58) Field of Search ............................. 623/17.11, 17.15, 623/17.16

(56) References Cited

U.S. PATENT DOCUMENTS

| | | | |
|---|---|---|---|
| 5,653,763 | * | 8/1997 | Errico et al. ....................... 623/17.11 |
| 5,702,453 | * | 12/1997 | Rabee et al. ....................... 623/17.11 |
| 5,766,253 | * | 6/1998 | Brosnahan, III ................... 623/17.11 |
| 5,876,457 | * | 3/1999 | Picha et al. ........................ 623/17.11 |
| 5,916,267 | * | 6/1999 | Tienboon ........................... 623/17.11 |
| 5,968,098 | * | 10/1999 | Winslow ............................. 623/17.11 |

FOREIGN PATENT DOCUMENTS

| | | |
|---|---|---|
| 44 16 605 | 6/1995 | (DE) . |
| 296 12 269 U | 10/1996 | (DE) . |
| 0 369 603 | 5/1990 | (EP) . |
| 0 664 994 | 8/1995 | (EP) . |
| WO 95/08964 | 4/1995 | (WO) . |
| WO 97/15246 | 5/1997 | (WO) . |

* cited by examiner

Primary Examiner—David H. Willse
Assistant Examiner—Suzette J. Jackson
(74) Attorney, Agent, or Firm—Barry R. Lipsitz; Douglas M. McAllister

(57) ABSTRACT

In order, in the case of an implant for vertebral body fusion having a support body, which comprises two opposite-lying support surfaces for application against the opposing end faces of the vertebral bodies to be fused and is insertable into the gap between the two adjacent vertebral bodies, to achieve an optimum fixing of the supporting body in the intervertebral space, it is proposed that the supporting body has at least one location channel, which extends between the support surfaces and is open at its top and bottom side, and that there is insertable into the location channel a fixing element provided with an external projection and guided in the location channel so as to be rotatable about its longitudinal axis, which fixing element once inserted into the location channel projects out of the open location channel in that it protrudes at the top and bottom side of the supporting body beyond the support surfaces.

30 Claims, 4 Drawing Sheets

IMPLANT FOR VERTEBRAL BODY FUSION

Figure 1:
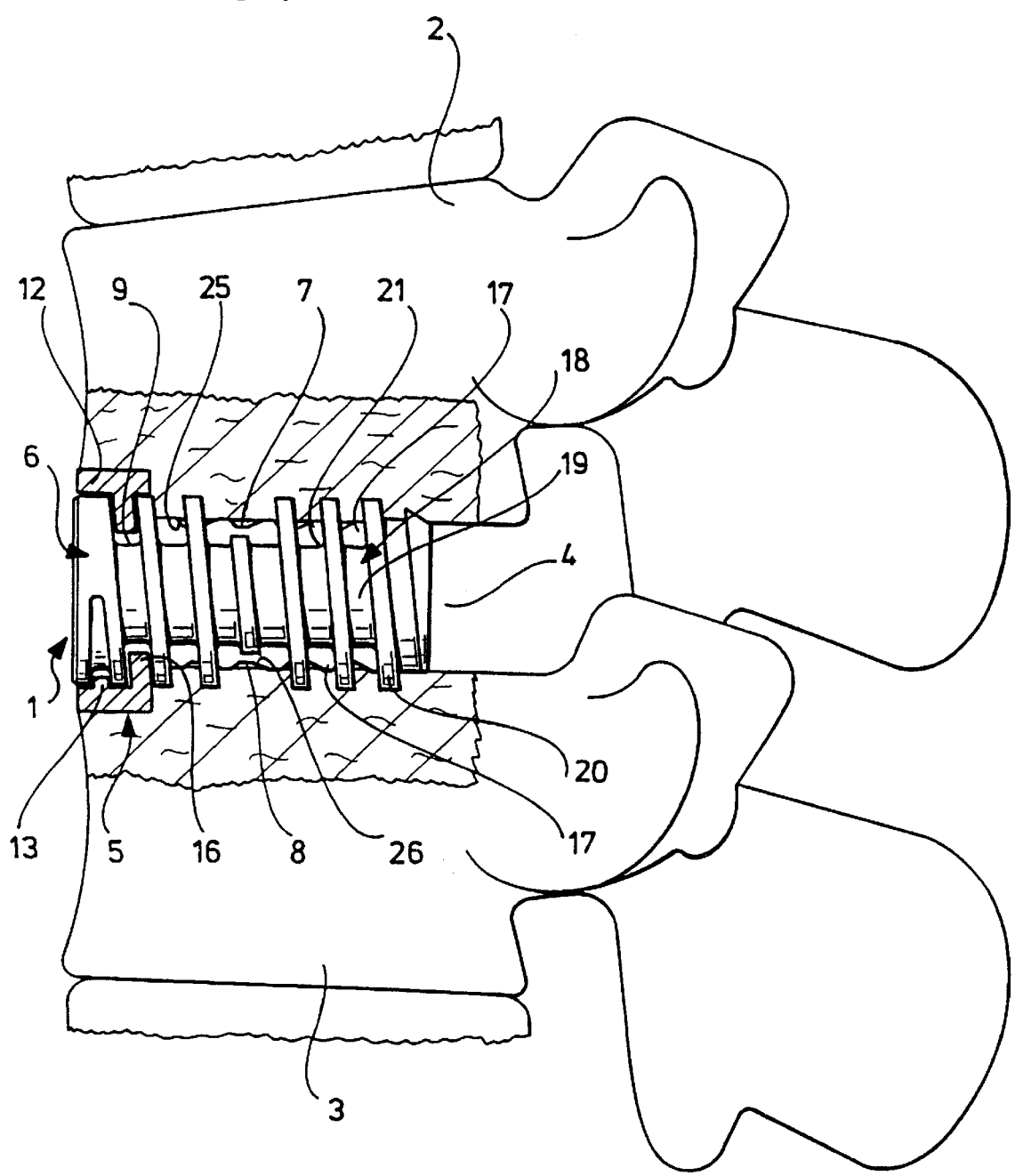

This application is a continuation of PCT/EP97/03730 filed Jul. 12, 1997.

The present invention relates to the subject matter disclosed in international application PCT/EP 97/03730 of Jul. 12, 1997, the entire specification of which is incorporated herein by reference.

The invention relates to an implant for vertebral body fusion having a supporting body, which comprises two opposite-lying support surfaces for application against the opposing end faces of the vertebral bodies to be fused and is insertable into the gap between the two adjacent vertebral bodies.

In the event of damage to intervertebral disks, it is frequently necessary to remove said disks and join the adjacent vertebral bodies permanently to one another. In order to achieve this, it is known to insert a supporting body, which is substantially cuboidal or wedge-shaped, in place of the removed intervertebral disk into the intervertebral space, where it is intended to take over the supporting and spacing function of the intervertebral disk (WO 95/08964).

In order in such a case to achieve a relatively secure fixing of the supporting body in the intervertebral space, the latter has to be highly profiled and this creates problems with the insertion.

On the other hand, it is also known to insert laterally into the intervertebral space a hollow cylindrical bone-screw, which then engages into shell-shaped internal thread regions of the two vertebral bodies and hence mutually fixes the latter. Such a bone-screw is locked against axial displacement but because of the relatively low surface contact high pressure loads arise, which may sometimes lead to the implant in the form of a bone-screw sinking into the vertebral body (EP 0369603 A1).

The object of the invention is to provide an implant which, on the one hand, is easy to insert and, on the other hand, after insertion is locked against displacement.

In the case of an implant of the type described initially, said object is achieved according to the invention in that the supporting body has at least one location channel, which extends between the support surfaces and is open at its top and bottom side, and that there is insertable into the location channel a fixing element provided with an external projection and guided in the location channel so as to be rotatable about its longitudinal axis, which fixing element once inserted into the location channel projects out of the open location channel in that it protrudes at the top and bottom side of the supporting body beyond the support surfaces.

What is proposed, therefore, is a two-part implant substantially comprising a supporting body, which lies with its support surfaces against the end faces of the vertebral bodies and hence provides a mutual supporting of said vertebral bodies over a large area. In addition, a fixing element is provided, which protrudes in an upward and downward direction from said supporting body and hence engages positively into correspondingly shell-shaped recesses of the vertebral bodies.

A substantial portion of the supporting forces is taken over in said construction by the supporting body, with the fixing element also playing a limited role in said regard, but the important point is that the fixing element as a result of the positive engagement with the two vertebral bodies is non-displaceable relative to said vertebral bodies. By virtue of the accommodation of the fixing element in the location channel, the supporting body is also fixed relative to the vertebral bodies.

While it is possible in principle for the fixing element to be guided and hence fixed only in transverse direction in the location channel, in a preferred embodiment means are provided, which fix the fixing element inserted into the location channel in axial direction in said location channel. Said means therefore connect the fixing element and the supporting body also in axial direction, and as a result the supporting body is also fixed in axial direction so as to be non-displaceable relative to the vertebral bodies.

The fixing element is supported rotatably in the location channel, the positive engagement with the vertebral bodies being produced through rotation of the fixing element. In said case, the fixing element might carry for example, in the manner of a key, a bit-shaped projection which, in one angular position of the fixing element, does not protrude beyond the support surfaces so that the supporting body may be inserted into the intervertebral space, whereas by rotating the fixing element said projections are raised above the support surfaces and hence engage positively into the adjacent vertebral bodies. With such a fixing element, a key-like locking is achieved upon rotation of the fixing element.

According to another preferred embodiment, it is provided that the fixing element takes the form of a bone-screw.

Such a bone-screw may be fixed relative to the supporting body in various ways, e.g. a pin penetrating the bone-screw and the supporting bodies might be inserted after the bone-screw has been screwed in.

It is particularly advantageous when, according to a preferred embodiment of the invention, it is provided that the means of fixing the bone-screw in axial direction comprise an internal thread in the location channel, which matches the external thread of the bone-screw. With such a solution, therefore, the bone-screw is screwed into the location channel and at the same time a screwing into the adjacent vertebral bodies is effected, with it being possible to use in the latter a prefabricated internal thread. In principle, it would however also be possible to design the bone-screw in a self-cutting manner so that it itself produces a corresponding thread in the vertebral body.

In a preferred embodiment, it is provided that the location channel separates the parts of the supporting body, which are disposed on either side of the location channel, from one another and that said parts are connected to one another by a bridge.

Said bridge may be, for example, a web which connects the two parts and lies opposite the insertion end of the location channel.

In another embodiment, it may be provided that the bridge is disposed at the insertion end of the location channel and has an insertion opening for the fixing element. It is advantageous when the location channel extends substantially over the entire depth of the supporting body, thereby creating the possibility of inserting a long fixing element, which over a large portion of said length is in engagement with the adjacent vertebral bodies.

In principle, it is possible to provide only a single location channel in the supporting body, preferably in the centre of the latter, although it would in principle also be possible to dispose a plurality of location channels alongside one another in the supporting body, e.g. to dispose symmetrically relative to the centre line two such location channels each receiving a corresponding fixing element.

The support surfaces may be formed parallel to one another, although it is in principle also possible for said support surfaces to be inclined towards one another so that the support surfaces are adapted to the geometry of the end faces of the vertebral bodies, particularly when it is necessary for the vertebral bodies to be inclined in a specific manner towards one another.

In a preferred embodiment, it is provided that the support surfaces are profiled, e.g. the supporting surfaces may carry ribs extending transversely to the longitudinal direction of the location channel. This is of considerable assistance in fixing the supporting bodies in the intervertebral space and ensures a permanent intimate connection between bone tissue and support surface.

In said case, it is particularly advantageous when the supporting surfaces are provided with a bone-friendly surface coating which promotes growing-in of the bone material.

For said purpose, recesses for bone tissue to grow into may also be disposed in the support surfaces.

In a particularly simple refinement, the supporting body is substantially cuboidal in shape.

The bone-screws may in principle be of any desired design although it is particularly advantageous when the bone-screws are hollow and have holes in their lateral surface. Such bone-screws may be filled with bone material and enable the bone filling at the inside and the vertebral body at the outside of the bone-screws to knit through the holes. Thus, a bony bridge between the vertebral bodies may grow through the bone-screw, with the result that an implant of said type, on the one hand, provides optimum large-area support by means of the supporting body and, on the other hand, also produces a biological fusion of the vertebral bodies by means of the bony bridge in the region of the bone-screw.

In said case, it is advantageous when the holes are produced by elongate axial cuts in the wall of the bone-screw, which penetrate the wall only in the region of the valleys of the external thread. The internal cross section of the bone-screw may, in a preferred embodiment, comprise a coaxial, circular region adjoined at opposite sides by two parallel, strip-like portions, which extend tangentially relative to the circular region. Said strip-like regions may project laterally from the circular region. In said case, it is advantageous when the strip-like regions terminate substantially in semicircles at their end. It has emerged that, by said means, the bone-screw remains flexible to a slight extent without being mechanically damaged by the bending stress. This is extraordinarily important because, as a result of a slight flexibility of the bone-screw, the bone material growing through is mechanically stressed, and said mechanical stress promotes the bone growth.

In another preferred embodiment of the invention, it is provided that the bone-screw has a core, the outside diameter of which is smaller than the clearance or spacing of the walls of the location channel, thereby forming between said walls and the core a gap which is penetrated by the thread turns of the bone-screw. In said case, the core is of a particularly solid design.

Given such a refinement, the gap between the wall of the location channel, on the one hand, and the core, on the other hand, may be completely filled with bone material which enables a knitting together of the two adjacent vertebral bodies. The bone material is in said case fixed and supported by the thread turns of the bone-screw, which are situated in the gap, so that undesirable displacements of the bone material may be prevented.

The supporting body and/or the fixing elements preferably made of titanium or a high-strength titanium alloy.

In principle, it is however also possible for said components to be made of plastic material, in particular of carbon-fibre-reinforced plastic material or a resorbable plastic material.

In another embodiment, it is provided that the supporting body is made of bone material or artificial bone material. In said case, it is advantageous when the fixing element is made of resorbable plastic material. Given such a refinement, the supporting body itself becomes part of the bony bridge between the two vertebral bodies, the space occupied by the fixing element being gradually released by the fixing element upon the latter's resorption and then being filled likewise as a result of bone growth.

Figure 2:
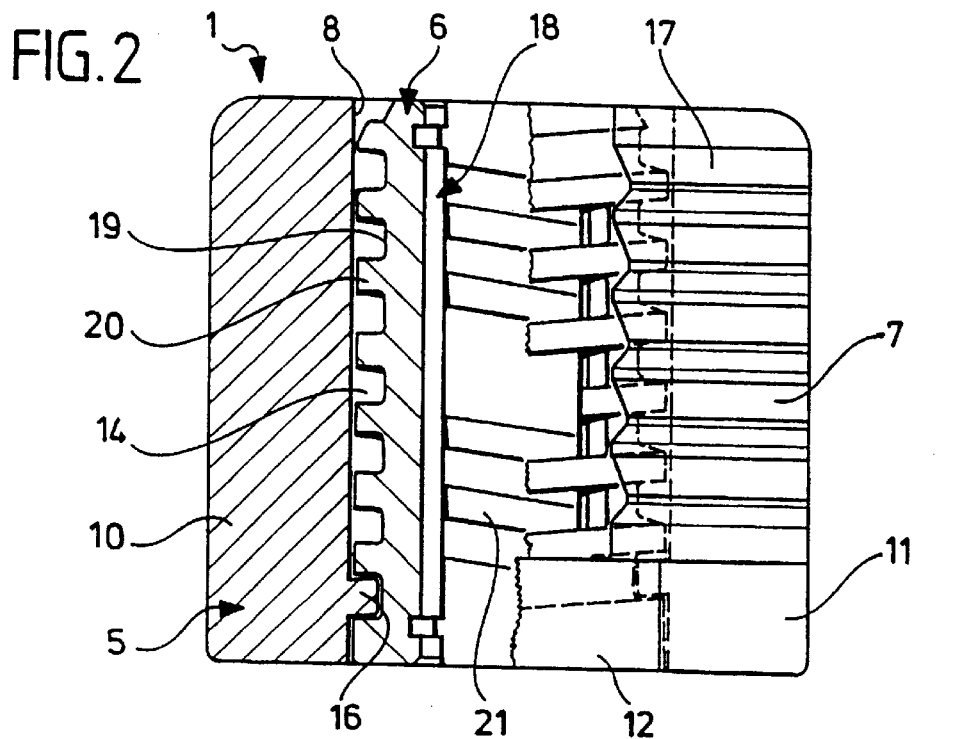
Figure 3:
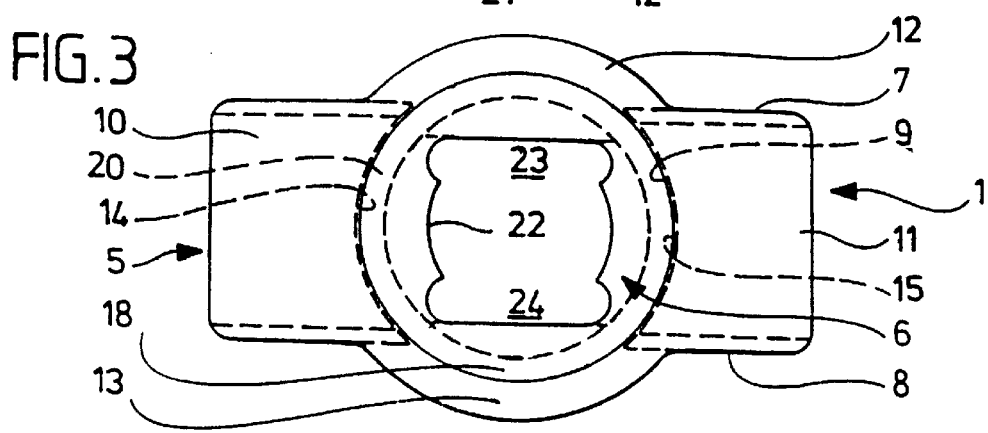

The following description of preferred embodiments serves, in conjunction with the drawings, to provide a more detailed explanation. The drawings show:

FIG. 1: a cross-sectional view through two vertebral bodies with an inserted intervertebral implant according to a first preferred embodiment;

FIG. 2: a plan view of the implant of FIG. 1, one half being cut open parallel to a support surface;

FIG. 3: a view of the implant of FIG. 1 from the insertion side and

Figure 4:
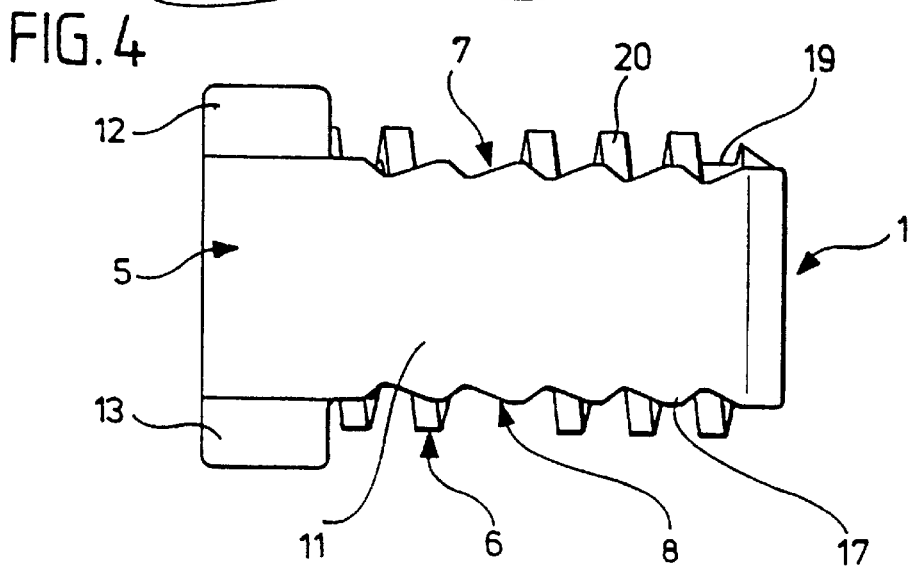
Figure 5:
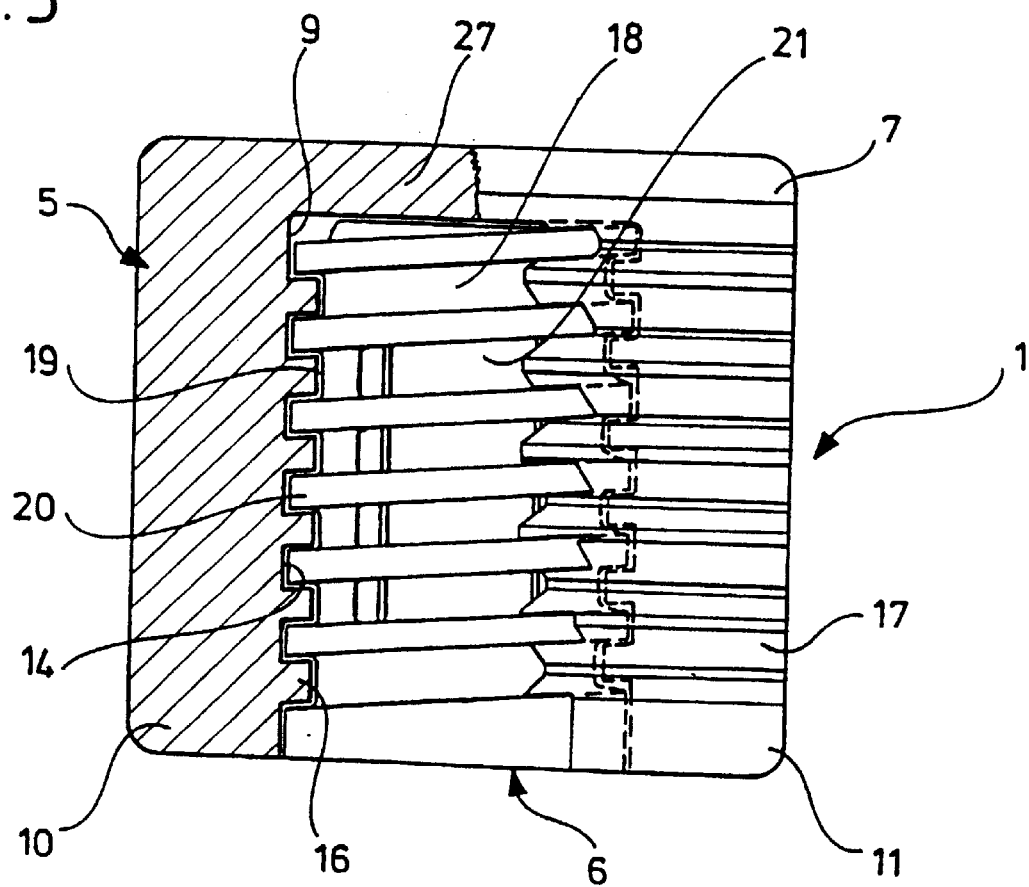
Figure 6:
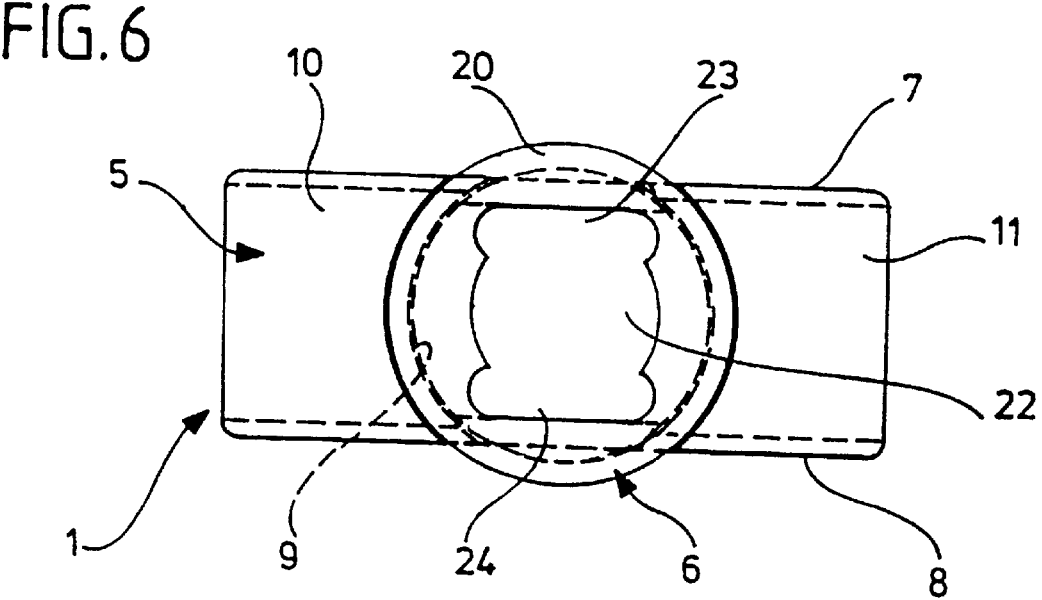
Figure 7:
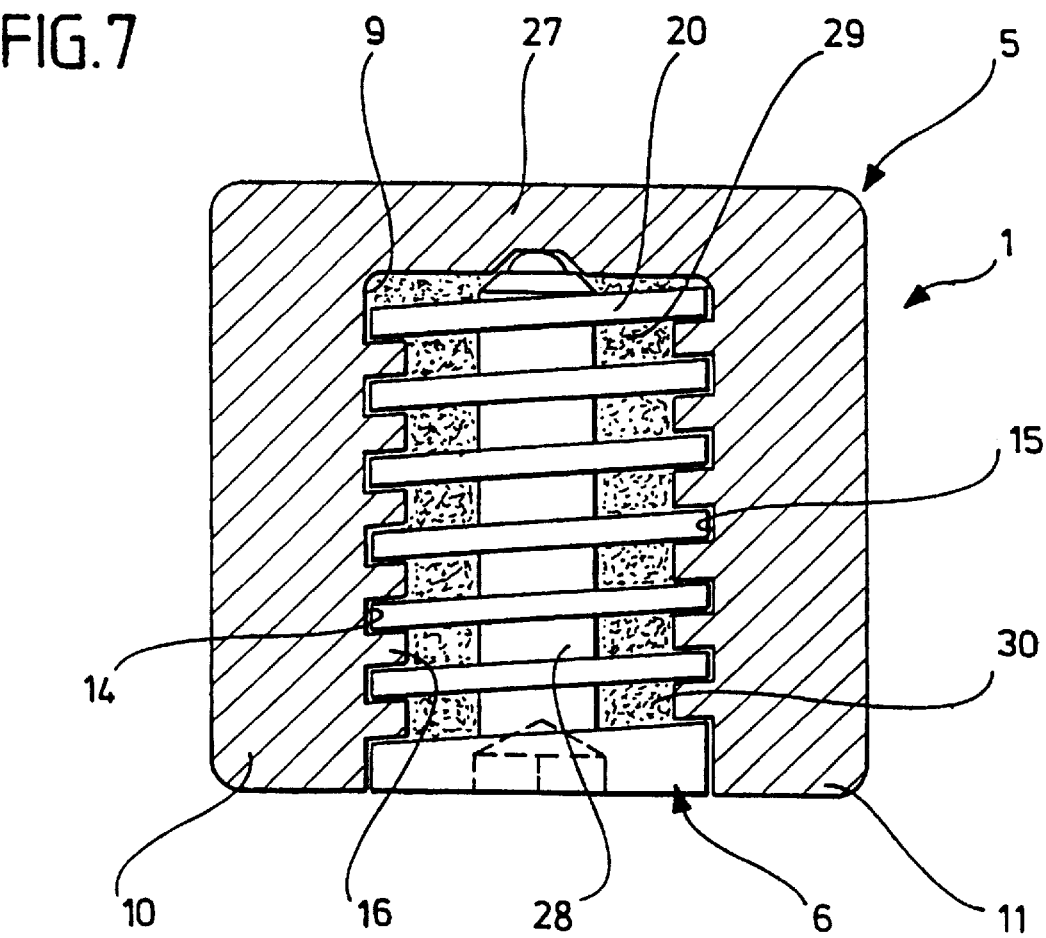
Figure 8:
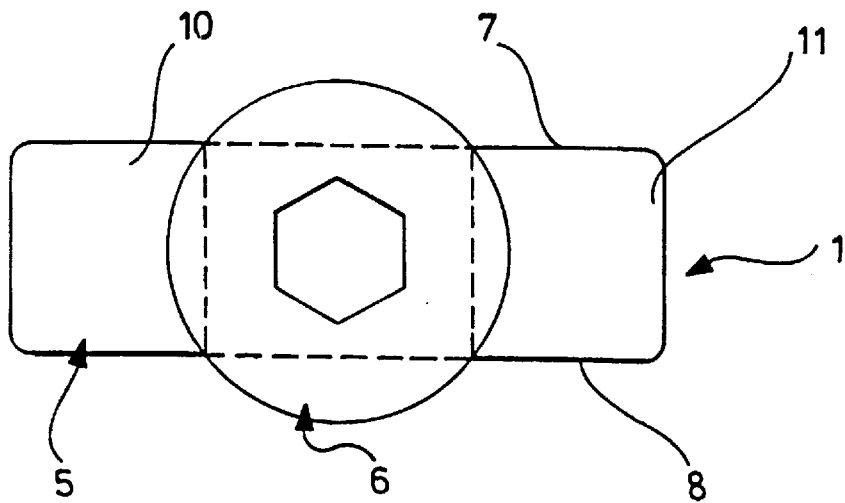

FIG. 4: a side view of the implant of FIG. 1;

FIG. 5: a view similar to FIG. 2 of a modified embodiment of an implant;

FIG. 6: a view similar to FIG. 3 of the implant of FIG. 5;

FIG. 7: a view similar to FIG. 2 of a modified embodiment of an implant with a bone-screw having a small-diameter core and FIG. 8: a view similar to FIG. 3 of the implant of FIG. 7.

The implant 1 illustrated in the drawings is inserted into the intervertebral space 4 between two vertebral bodies or vertebrae 2, 3 in such a way that it replaces the previously removed intervertebral disk and connects the adjacent vertebral bodies 2 and 3 into a unit, in the manner illustrated in FIG. 1.

The implant 1 comprises two parts, namely a substantially cuboidal supporting body 5 and a bone-screw 6 inserted into said supporting body.

The supporting body 5 at its top and bottom side comprises support surfaces 7, 8, which are substantially flat and parallel to one another, and in terms of its lateral dimensions extends over a substantial portion of the intervertebral space 4.

In the middle of the supporting body 5 the latter has, extending parallel to the support surfaces 7 and 8 and fully penetrating the supporting body 5, a location channel 9 of a circular cylindrical cross section which is so dimensioned that it is open at the top and bottom side. Said location channel 9 therefore divides the supporting body 5 into two parts 10, 11, which are connected to one another by two arc-shaped webs 12, 13 at the top and bottom side of the supporting body 5. Said arc-shaped webs 12 and 13 together form an opening 14, which is aligned with the location channel 9.

Situated in the interior of the location channel 9, which is actually formed only by two inner walls 14, 15 of the parts 10, 11 of an arc-shaped cross section, is an internal thread which, in the illustrated embodiment of FIGS. 1 and 4, is formed by a single thread turn 16 in the insertion region of the location channel 9.

The support surfaces 7 and 8 are profiled by means of ribs 17, extending at right angles to the longitudinal direction of the location channel 9, and the surface may moreover be coated with a bone-friendly material in the manner generally customary when fitting prostheses and implants.

The bone-screw 6 inserted into the location channel 9 is a cylindrical hollow body 18, which has a continuous thread turn 20 provided on its outer wall 19. The interior of said hollow body 18 communicates via holes 21 in the outer wall 19 with the exterior; the holes 21 are however limited to the region between the projections of the thread turn 20. The cross-sectional shape of the interior of the hollow body 18 may be described by a circular, coaxial inner region 22 and by strip-shaped regions 23, 24, which tangentially adjoin said circular region 22 at opposite sides, extend parallel to one another, project laterally from the circular region 22 and terminate in a semicircular shape (FIG. 3). It has emerged that such a cross-sectional shape offers the possibility of, on the one hand, cutting holes laterally into the outer wall 19 of the hollow body 18 at the strip-shaped regions 23 and 24 between the thread turns 20 while, on the other hand, maintaining such a high mechanical stability that the bone-screw 6, despite being slightly flexible, is in no way damaged by said mechanical deformation.

The thread turn 20 has an outside diameter corresponding to the inside diameter of the inner walls 14 and 15 so that the bone-screw guided in the location channel 9 formed by the inner walls 14 and 15 is rotatable, the thread turns 20 and to a slight extent also the outer wall 19 protruding beyond the support surfaces 7 and 8.

For insertion of the implant, first the damaged intervertebral disk is removed and, optionally, the end faces 25 and 26 of the vertebral bodies 2 and 3 are also machined using suitable instruments.

The supporting body 5 is then inserted into the intervertebral space.

It is then possible to insert into the still empty location channel 9 a drilling or cutting tool, which works shell-shaped or dished recesses into the end faces 25 and 26 of the vertebral bodies 2 and 3, which recesses together with the inner walls 14 and 15 of the location channel 9 form the location channel 9, the inside diameter of said shells however being smaller than the inside diameter of the inner walls 14 and 15.

A thread corresponding to the thread of the bone-screw 6 may then be cut into said shell-shaped recesses of the vertebral bodies 2 and 3.

After said preparation of the vertebral bodies, the bone-screw 6 is inserted and screwed into the location channel 9, the thread turn 20 simultaneously engaging into the thread of the vertebral bodies 2 and 3. By said means, a locking of the supporting body 5 in the intervertebral space 4 is effected.

The bone-screw 6 is filled with bone material and therefore forms a bony bridge between the two vertebral bodies 2 and 3 so that the bone material of the vertebral bodies may grow through the holes 21 in the outer wall 19 into the interior of the bone-screw 6.

In principle, the surgeon has the option of using the supporting body 5 also without a bone-screw 6 should he, in specific cases, wish to achieve an adequate fixing of the supporting body 5 in another manner.

Furthermore, it is also possible to implant the bone-screw 6 without the supporting body 5 in the manner known as such for bone-screws.

The described implant therefore offers the surgeon the possibility of either utilizing the particularly advantageous effects of the combined implant or making separate use of the two parts of the implant, should he consider this necessary.

As the implant illustrated in FIGS. 5 and 6 substantially corresponds to the implant of FIGS. 1 to 4, parts which are identical to one another are characterized by the same reference characters.

Unlike the supporting body 5 of FIGS. 1 to 4, here the two parts 10 and 11 are connected, not by arc-shaped webs 12 and 13 at the insertion end of the location channel 9, but by a web 27 at the opposite end of the location channel 9. Said web 27 closes the location channel 9 at said end, with the added result that the depth of insertion of the bone-screw 6 is delimited.

In the embodiment of FIGS. 7 and 8, in which identical parts again bear the same reference characters, the bone-screw 6 is provided with a solid core 28 which carries the thread turn 20. The outside diameter of the core 28 is much smaller than the spacing of the opposing walls 14 and 15 of the location channel 9, thereby creating a gap 29 between the core 28 and the walls 14, 15. Said gap 29 may, once the bone-screw has been inserted, be completely filled with bone material 30 so that said bone material forms a bondy bridge between the vertebral bodies which are to be fused. The bone material 30 is in said case fixed between the adjacent turns of the thread turn 20.

What is claimed is:

1. Implant for vertebral body fusion having a supporting body, which comprises two opposite-lying support surfaces for application against the opposing end faces of the vertebral bodies to be fused and is insertable into the gap between the two adjacent vertebral bodies, characterized in that the supporting body (5) has at least one location channel (9), which extends between the support surfaces (7, 8) and is open at its top and bottom side, and that there is insertable into the location channel (9) a fixing element (6) provided with an external projection (20) and guided in the location channel (9) so as to be rotatable about its longitudinal axis, which fixing element once inserted into the location channel (9) projects out of the open location channel (9) in that it protrudes at the top and bottom side of the supporting body (5) beyond the support surfaces (7, 8).

2. Implant according to claim 1, characterized in that means are provided, which fix the fixing element (6) inserted into the location channel (9) in axial direction in said location channel.

3. Implant according to claim 1, characterized in that the fixing element is a bone-screw (6).

4. Implant according to claim 2, characterised in that the fixing element is a bone screw (6).

5. Implant according to claim 3, characterized in that the means of fixing the bone-screw (6) in axial direction comprise an internal thread (16) in the location channel (9), which matches an external thread (20) of the bone-screw (6).

6. Implant according to claim 1, characterized in that the location channel (9) separates the parts (10, 11) of the supporting body (5), which are disposed on either side of the location channel, from one another and that said parts (10, 11) are connected to one another by a bridge (12, 13; 27).

7. Implant according to claim 6, characterized in that the bridge is a web (27), which connects the two parts (10, 11) and lies opposite the insertion end of the location channel (9).

8. Implant according to claim 7, characterized in that the web (27) closes the location channel (9) at the end remote from the insertion end.

9. Implant according to claim 6, characterized in that the bridge (12, 13) is disposed at the insertion end of the location channel (9) and has an insertion opening for the fixing element (6).

10. Implant according to claim 1, characterized in that the location channel (9) extends substantially over the entire depth of the supporting body (5).

11. Implant according to claim 1, characterized in that a plurality of location channels (9) are disposed alongside one another in a supporting body (5).

12. Implant according to claim 1, characterized in that the support surfaces (7, 8) are inclined towards one another.

13. Implant according to claim 1, characterized in that the support surfaces (7, 8) are profiled.

14. Implant according to claim 13, characterized in that the support surfaces (7, 8) carry ribs (17) extending transversely to the longitudinal direction of the location channel (9).

15. Implant according to claim 1, characterized in that the support surfaces (7, 8) are provided with a bone-friendly surface coating.

16. Implant according to claim 1, characterized in that recesses, into which bone tissue may grow, are disposed in the support surfaces (7, 8).

17. Implant according to claim 1, characterized in that the supporting bodies (5) are substantially cuboidal in shape.

18. Implant according to claim 3, characterized in that the bone-screws (6) are hollow and have holes (21) in their lateral surface.

19. Implant according to claim 18, characterized in that the holes (15) are produced by elongate axial cuts in the wall (19) of the bone-screw (6), which penetrate the wall (19) only in the region of the valleys of the external thread (20).

20. Implant according to claim 18, characterized in that the internal cross section of the bone-screw (6) comprises a coaxial circular region (22) adjoined at opposite sides by two parallel, strip-shaped portions (23, 24), which extend tangentially relative to the circular region (22).

21. Implant according to claim 20, characterized in that the strip-shaped regions (23, 24) project laterally from the circular region (22).

22. Implant according to claim 20, characterized in that the strip-shaped regions (23, 24) terminate substantially in semicircles at their end.

23. Implant according to claim 3, characterized in that the bone-screw (6) has a core (28), the outside diameter of which is smaller than the spacing of the walls (14, 15) of the location channel (9), thereby forming between said walls (14, 15) and the core (28) a gap (29) which is penetrated by the thread turns (20) of the bone-screw (6).

24. Implant according to claim 23, characterized in that the core (28) is solid.

25. Implant according to claim 1, characterized in that the supporting body (5) and/or the fixing element (6) are/is made of titanium or a titanium alloy.

26. Implant according to claim 1, characterized in that the supporting body (5) and/or the fixing element (6) are/is made of plastic material.

27. Implant according to claim 26, characterized in that the supporting body (5) and/or the fixing element (6) are/is made of carbon-fibre-reinforced plastic material.

28. Implant according to claim. 26, characterized in that the supporting body (5) and/or the fixing element (6) are/is made of a resorbable plastic material.

29. Implant according to claim 1, characterized in that the supporting body (5) is made of bone material or artificial bone material.

30. Implant according to claim 29, characterized in that the fixing element (6) is made of resorbable plastic material.

* * * * *